(12) United States Patent
Lamash et al.

(10) Patent No.: US 10,970,836 B2
(45) Date of Patent: Apr. 6, 2021

(54) SPECTRAL IMAGE DATA PROCESSING (71) Applicant: KONINKLIJKE PHILIPS N.V., Eindhoven (NL)

(72) Inventors: Yechiel Lamash, Haifa (IL); Liran Goshen, Pardes-Hanna (IL); Raz Carmi, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1329 days.

(21) Appl. No.: 15/103,985

(22) PCT Filed: Dec. 3, 2014

(86) PCT No.: PCT/IB2014/066540
§ 371 (c)(1),
(2) Date: Jun. 13, 2016

(87) PCT Pub. No.: WO2015/092588
PCT Pub. Date: Jun. 25, 2015

(65) Prior Publication Data
US 2016/0321803 A1 Nov. 3, 2016

Related U.S. Application Data

(60) Provisional application No. 61/916,850, filed on Dec. 17, 2013.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/7275* (2013.01); *A61B 6/032* (2013.01);
(Continued)

(58) Field of Classification Search
CPC ....... G06T 7/0012; G06T 2207/201116; G06T 2211/408; A61B 6/032; A61B 6/504;
(Continued)

(56) References Cited

U.S. PATENT DOCUMENTS 7,903,860 B2 3/2011 Grasruck
7,990,379 B2 8/2011 Aharon
(Continued)

FOREIGN PATENT DOCUMENTS

CN 102737376 10/2012
EP 2357609 8/2011
(Continued)

OTHER PUBLICATIONS

Saba, et al., "Maximizing quantitative accuracy of lung airway lumen and wall measure obtained from X-ray CT imaging", J. Appl. Physiol. (2003).
(Continued)

*Primary Examiner* — Boniface N Nganga
(74) *Attorney, Agent, or Firm* — Larry Liberchuk (57) ABSTRACT

A method includes obtaining contrast enhanced spectral image data that includes voxels representing a tubular structure. The method further includes generating at least a contrast map based on the obtained contrast enhanced spectral image data. The method further includes generating an updated contrast map based on a spectral model. The method further includes segmenting the tubular structure based on updated contrast map. A computing system (120) includes a spectral analyzer (202) that receives contrast enhanced spectral image data and generates a spectral analysis data based thereon, wherein the spectral analysis data includes a contrast map, The computing system further includes a spectral analysis data processor (204) that refines the spectral analysis data, generating refined spectral analysis data.

20 Claims, 7 Drawing Sheets

(51) Int. Cl.
    A61B 6/03      (2006.01)
    A61B 6/00      (2006.01)
(52) U.S. Cl.
    CPC .............. *A61B 6/504* (2013.01); *A61B 6/507*
        (2013.01); *A61B 6/5205* (2013.01); *A61B*
        *6/5217* (2013.01); *G06T 2207/20116*
        (2013.01); *G06T 2207/30101* (2013.01); *G06T*
        *2211/408* (2013.01)
(58) Field of Classification Search
    CPC ..... A61B 6/507; A61B 6/5205; A61B 6/5217;
                                              A61B 5/7275
    See application file for complete search history.

(56)                References Cited

U.S. PATENT DOCUMENTS

| | | | |
|---|---|---|---|
| 8,355,550 B2 | 1/2013 | Zhang | |
| 2007/0031019 A1 | 2/2007 | Lesage | |
| 2008/0240527 A1* | 10/2008 | Keller | G06K 9/00127 |
| | | | 382/128 |
| 2009/0161939 A1 | 6/2009 | Wu | |
| 2011/0103542 A1* | 5/2011 | Allmendinger | A61B 6/507 |
| | | | 378/4 |
| 2012/0308106 A1 | 12/2012 | Kelly | |
| 2013/0267846 A1 | 10/2013 | Patwardhan | |
| 2015/0003694 A1* | 1/2015 | Beymer | G06T 5/002 |
| | | | 382/128 |

FOREIGN PATENT DOCUMENTS

| | | | | |
|---|---|---|---|---|
| JP | 2012245235 | | 12/2012 | |
| WO | 2013/011418 | | 1/2013 | |
| WO | WO-2013075127 A1 * | 5/2013 | ............. | G16H 40/20 |
| WO | WO-2014091339 A1 * | 6/2014 | ............. | A61B 90/39 |

OTHER PUBLICATIONS

Holtzman-Gazit, et al., "Segmentation of thin structures in volumetric medical images", IEEE Transactions on Image Processing, 2006.

Lesage, et al., "A review of 3D vessel lumen segmentation techniques: Models, features and extraction schemes", Medical image analysis 13.6 (2009): 819-845.

Carmi, et al., "Experimental evaluation of image-based spectral analysis method for multi energy window photon counting X-ray CT", 2008 IEEE Nuclear Science Symposium Conference Record.

Biermann, et al., "Evaluation of Computer-Assisted Quantification of Carotid Artery Stenosis", Journal of Digital Imaging; Jul. 23, 2011.

Yang, et al., "Automatic centerline extraction of coronary arteries in coronary computed tomographic angiography." The International Journal of Cardiovascular Imaging 28.4 (2012): 921-933.

Tonino, et al., "Fractional flow reserve versus angiography for guiding percutaneous coronary intervention" N Eng J Med. 2009;360:213-224.

Fearon, et al., "Economic evaluation of fractional flow reserve-guided percutaneous intervention in patients with multivessel disease", Circulation. 2010;122:2545-2550.

Kim et al., "Patient-Specific Modeling of Blood Flow and Pressure in Human Coronary Arteries". Annals of Biomedical Engineenng, vol. 38, No. 10, Oct. 2010, pp. 3195-3209.

Taylor, et al., "Patient-Specific Modeling of Cardiovascular Mechanics", Annual Review of Biomedical Engineering, vol. 11: 109-134, Aug. 2009.

Kawasaki, et al., "Prediction of acute coronary syndrome by using multislice computed tomography.—Can we predict the onset of acute coronary syndrome? (Pro)-" Circ. J., vol. 75, pp. 2013-2018; discussion 2026, Jul. 25, 2011.

Liang, et al., "Calcium de-blooming in coronary CT image", Bioinformatics and Bioengineering, 2007. BIBE 2007. Proceedings of the 7th IEEE International Conference on, 2007, pp. 257-262.

Thomas, et al., "Automatic lumen segmentation in calcified plaques: dual-energy CT versus standard reconstructionsn in comparison with digital subtraction angiography" AJR (2010).

Kirbas, et al., "A review of vessel extraction techniques and algorithms", ACM Computing Surveys, vol. 36, pp. 81-121, 2004.

Bouraoui, et al., "Fully automatic 3D segmentation of coronary arteries based on mathematical morphology", IEEEinternational symposium biomedical imaging: from nanoto macro (ISBI) 1059-1062.

Zambal, et al., "Shape and appearance models for automatic coronary artery tracking" The Midas Journal—2008 MICCAI Workshop Grand Challenge Coronary Artery Tracking.

Tek, et al., "Automatic coronary tree modeling", The Midas Journal—2008 MICCAI Workshop Grand Challenge Coronary Artery Tracking.

Wang, et al., "An automatic seeding method for coronary artery segmentation and skeletonization in CTA", The Midas Journal—2008 MICCAI Workshop Grand Challenge Coronary Artery Tracking.

Bauer, et al., "Edge based tube detection for coronary artery centerline extraction", The Midas Journal—2008 MICCAI Workshop Grand Challenge Coronary Artery Tracking.

Cai, et al., "Virtual Colon Tagging for Electronic Cleansing in Dual-energy Fecal-tagging CT Colonography", 34th Annual International Conference of the IEEE EMBS (2012.

Koo B-K et al., "Diagnosis of Ischemia-Causing Coronary Stenoses by Noninvasive Fractional Flow Reserve Computed from Coronary Computed Tomographic Angiograms", Results from the prospective multicenter Discover-Flow (Diagnosis of Ischemia-Causing Stenoses Obtained Via Noninvasive Fractional Flow Reserve) study, Journal of American College of Cardiology, Nov. 1, 2011, vol. 58, No. 19, pp. 1989-1997.

* cited by examiner

SPECTRAL IMAGE DATA PROCESSING

CROSS REFERENCE TO RELATED APPLICATIONS

This application is the U.S. National Phase application under 35 U.S.C. § 371 of International Application No. PCT/I82014/066540 filed Dec. 3, 2014, published as WO 2015/092588 on Jun. 25, 2015, which claims the benefit of U.S. Provisional Patent Application No. 61/916,850 filed Dec. 17, 2013. These applications are hereby incorporated by reference herein.

The following generally relates to spectral image data processing and is described with particular application to computed tomography (CT). However, the following is also amenable to other imaging modalities.

Computed tomography (CT) is a non-invasive imaging procedure. A CT scanner generally includes an x-ray tube mounted on a rotatable gantry opposite a detector array across an examination region. The rotatable gantry and hence the x-ray tube rotate around the examination region. The x-ray tube is configured to emit radiation that traverses the examination region and is detected by the detector array. The detector array, in response, generates and outputs projection data indicative of the detected radiation. The projection data is reconstructed to generate volumetric image data. The volumetric image data includes voxels represented as gray scale intensity values corresponding to relative radiodensity.

The gray scale values generally reflect the attenuation characteristics of the scanned subject and show structure such as anatomical structures within the scanned subject. Since the absorption of a photon by a material is dependent on the energy of the photon traversing the material, the detected radiation also includes spectral information, which provides additional information indicative of the elemental or material composition (e.g., atomic number) of the scanned material of the subject and/or object. Unfortunately, with a not-spectral CT scanner, the projection data output by the detector array is proportional to the energy fluence integrated over the energy spectrum and thus does not reflect the spectral characteristics.

A CT scanner configured for spectral (multi-energy) imaging captures the above-noted spectral characteristics. Generally, a CT scanner configured as such generates at least two attenuation values respectively corresponding to at least two different photon energy ranges. Such a scanner may include two or more x-ray tubes configured to emit radiation having different mean spectrums, a single x-ray tube configured to be controllably switched between at least two different emission voltages (e.g., 80 kVp and 140 kVp) during scanning, and/or a single broad spectrum x-ray tube and an energy-resolving detector array with energy-resolving detectors (e.g., with photon counting detectors, at least two sets of scintillators with different spectral sensitivities or responses, etc.) and discrimination electronics.

Coronary artery disease (CAD) can result in response to plaque building up on the inner walls of the arteries of the heart. Complications from CAD may include luminal narrowing (stenosis) or occlusion of the coronary arteries, which reduces blood flow to the heart, rupturing of vulnerable plaque, etc. The decision to perform coronary revascularization is best informed by delineating objective evidence of inducible myocardial ischemia. A current major determinant for revascularization in CAD patients suffering from chest pain is the percentage of luminal narrowing of the coronary vessel. Unfortunately, the stenosis percentage measurement may not be enough to provide sufficiently clear information for determining whether to perform coronary revascularization.

Fractional flow reserve (FFR) is the ratio of maximal, hyperemic, myocardial blood flow through a diseased artery to the blood flow in the hypothetical case of a normal artery. FFR is measured by the ratio between the pressure after and the pressure before a stenosis in a cardiac catheterization laboratory procedure. The literature states that in the FAME (Fractional Flow Reserve Versus Angiography for Multivessel Evaluation) study of 1,005 patients with multivessel CAD, FFR-guided revascularization, specifically reserving revascularization for ischemic lesions with an FFR<0.8, was associated with significantly lower rates of adverse events and placement of fewer coronary stents compared to patients undergoing an angiographically guided strategy.

Recently, a method to estimate the FFR using computational fluid dynamics from multi-slice CT image data was proposed. An estimation of the FFR based on the CT studies enables to derive valuable functional diagnostic information for the physicians noninvasively. A necessary condition for estimating FFR from cardiac CT data is accurate segmentation of the lumen geometry, especially in stenotic regions. Unfortunately, the limited resolution in cardiac CT images and the partial volume effect of the contrast agent with other biological materials such as calcifications and other plaque components degrade the lumen segmentation quality.

Acute coronary syndrome (ACS) refers to a group of symptoms attributed to obstruction of the coronary arteries. A clinical challenge for cardiologists is the detection and prevention of ACS such as acute myocardial infarction. Histo-pathological studies have shown that the cause of sudden death from acute coronary syndromes is the presence of ruptured plaques. Therefore, an effort has been made for identifying profiles of atherosclerotic lesions that are prone to rupture. Based on autopsy studies, the majority of culprit lesions are typically non-stenotic, contain a large necrotic core with a thin overlying fibrous cap, and induce expansive remodeling of the vascular segment.

Multi-slice computed tomography (MSCT) enables detection of atherosclerotic plaque and assessment of its composition and mechanical properties. Thus, cardiac CT may provide an effective means of detecting and preventing ACS's. However, accurate characterization of plaque using MSCT is still a challenge. One limitation is the blooming artifact resulting from hyper-dense objects such as calcified plaque. Calcium blooming results primarily from the limited spatial resolution of the CT system and from beam-hardening effect. This blurring effect results in an over-representation of the calcified regions and, correspondingly, underestimation of other plaque components.

Aspects described herein address the above-referenced problems and others.

The following describes an approach that improves tubular structure (e.g., the coronary artery lumen) segmentation using contrast enhanced spectral CT image data. This approach leverages a mutual relation between structure localization and segmentation and quantitative contrast-agent mapping by spectral analysis. Each of these can provide improved results by using the results of the other as prior information, and the approach alternates through one or more iterations, which can optimize the segmentation. The resulting segmentation can be used to improve at least CT fractional flow reserve analysis (CT-FFR) and Acute Coronary Syndrome risk assessment.

In one aspect, a method includes obtaining contrast enhanced spectral image data that includes voxels representing a tubular structure. The method further includes generating at least a contrast map based on the obtained contrast enhanced spectral image data. The method further includes generating an updated contrast map based on a spectral model. The method further includes segmenting the tubular structure based on updated contrast map.

In another aspect, a computing system includes a spectral analyzer that receives contrast enhanced spectral image data and generates a spectral analysis data based thereon, wherein the spectral analysis data includes a contrast map, The computing system further includes a spectral analysis data processor that refines the spectral analysis data, generating refined spectral analysis data.

In another aspect, a computer readable storage medium is encoded with computer readable instructions. The computer readable instructions, when executed by a processer, causes the processor to: refine an iodine map based on an iterative update that utilizes a mutual relation between localizing and segmenting a lumen and quantitative contrast-agent mapping by spectral analysis, thereby generating a refined iodine map, and segment structure of interest from the refined iodine map.

The invention may take form in various components and arrangements of components, and in various steps and arrangements of steps. The drawings are only for purposes of illustrating the preferred embodiments and are not to be construed as limiting the invention.

Figure 1:
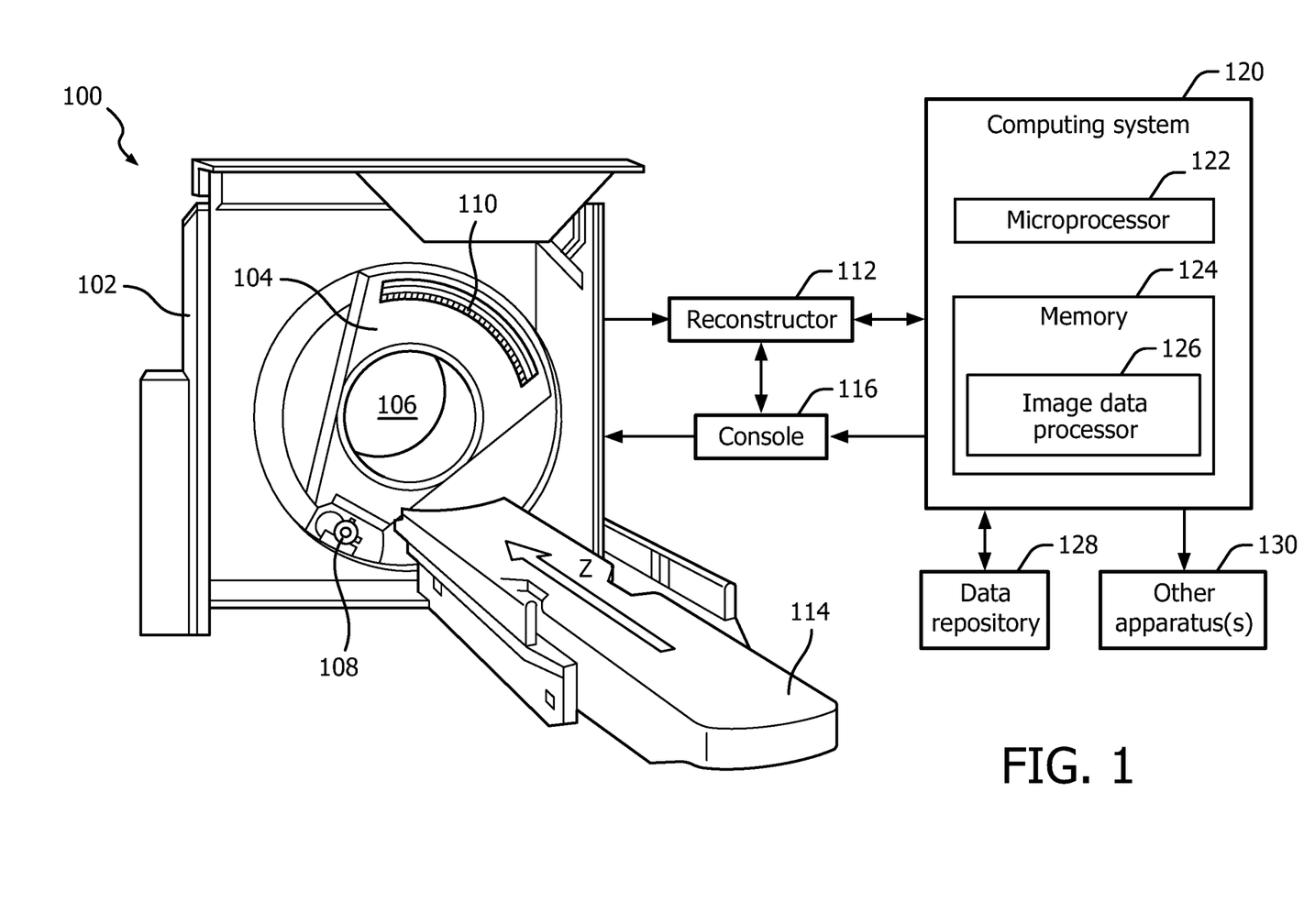
FIG. 1 schematically illustrates an example imaging system in connection with an image data processor.

Initially referring to FIG. 1, an imaging system 100 such as a computed tomography (CT) scanner is illustrated. The illustrated imaging system 100 is configured for spectral imaging. Spectral imaging, as utilized herein, refers to the imaging system 100 generating at least two attenuation values respectively corresponding to at least two different predetermined energy ranges. The imaging system 100 includes a generally stationary gantry 102 and a rotating gantry 104, which is rotatably supported by the stationary gantry 102 and rotates around an examination region 106 about a z-axis.

A radiation source 108, such as an x-ray tube, is rotatably supported by the rotating gantry 104 and rotates with the rotating gantry 104 and emits poly-energetic radiation that traverses the examination region 106. In one instance, the radiation source 108 includes a single broad spectrum tube. In a variation, the radiation source 108 is configured to be controllably switched between at least two different emission voltages (e.g., 80 kVp, 140 kVp, etc.) during scanning. The switching may be within an integration period, alternating between integration periods, between scans (e.g., a dual-spin scan in which a different kV is used for each successive scan), etc. In yet another variation, the radiation source 108 includes at least two tubes configured to emit radiation with different mean energy spectrums. Another variation includes a combination of the above.

A radiation sensitive detector array 110 subtends an angular arc opposite the radiation source 108 across the examination region 106. The radiation sensitive detector array 110 includes one or more rows of detectors, arranged parallel to each other along the z-axis. The radiation sensitive detector array 110 detects radiation traversing the examination region 106 and generates spectral projection data indicative thereof. Again, such projection data includes at least two attenuation values respectively corresponding to at least two different predetermined energy ranges and/or weights. In one instance, the radiation sensitive detector array 110 includes an energy resolving detector array, such as a multi-energy integrating detector with at least two scintillators having different x-ray energy sensitivities and at least two corresponding photosensors having corresponding optical sensitivities, a photon counting detector with a direct conversion material (e.g., CdTe, CdZnTe, etc.), and/or other energy resolving detector. In a variation, the radiation sensitive detector array 110 includes two different detection arrays corresponding to optional two different x-ray tubes at 108.

A reconstructor 112 reconstructs the spectral projection data output by the radiation sensitive detector array 110. This includes, for example, reconstructing the energy dependent components and generating one or more spectral images, each corresponding to a different energy value or range. The reconstructor 112 may also combine the energy dependent components and generate non-spectral image data. A subject support 114 such as a couch supports a subject or an object in the examination region 106. An operator console 116 includes a human readable output device such as a monitor and an input device such as a keyboard, mouse, etc. Software resident on the console 118 allows the operator to interact with and/or operate the imaging system 100, via a graphical user interface (GUI) or otherwise, for spectral imaging.

A computing system 120 includes at least one microprocessor 122 and a computer readable storage medium ("memory") 124. The memory 124 excludes transitory medium and includes physical memory and/or other non-transitory storage medium. The microprocessor 122 executes at least an image data processor 126 instruction(s) stored in the memory 124. The microprocessor 122 may also execute a computer readable instruction carried by a carrier wave, a signal or other transitory medium. The computing system 120 can be part of the console 118 and/or separate therefrom, as illustrated in FIG. 1.

The image data processor 126 instruction(s) includes an instruction(s) for processing at least contrast enhanced spectral image data. As described in greater detail below, in one instance, the image data processing instruction(s) includes instructions which process the contrast enhanced spectral image data in connection with segmenting tissue of interest represented in the contrast enhanced spectral image data. With respect to tubular structure segmentation (e.g., the lumen of a vessel such as a coronary artery and/or other vessel, such as a vessel of the brain, carotids, liver, lungs, and/or other vessel.), the image data processor 126 provides accurate segmentation of the geometry, including in constricted (e.g., stenotic) regions. As further described below, the instructions may also include instructions for other processing, that utilizes the segmentation.

The contrast enhanced spectral image data can be generated by and/or from the imaging system 100 and/or other imaging system. The spectral image data may alternatively be from a data repository 128 such as a picture archiving and communication system (PACS), an electronic medical record (EMR), a radiology information system (RIS), a hospital information system (HIS), and/or other data repository. The segmentation and/or results of the other processing can be stored in the console 116, the data repository 128, and/or other storage device, be conveyed to another apparatus 130, etc.

Figure 2:
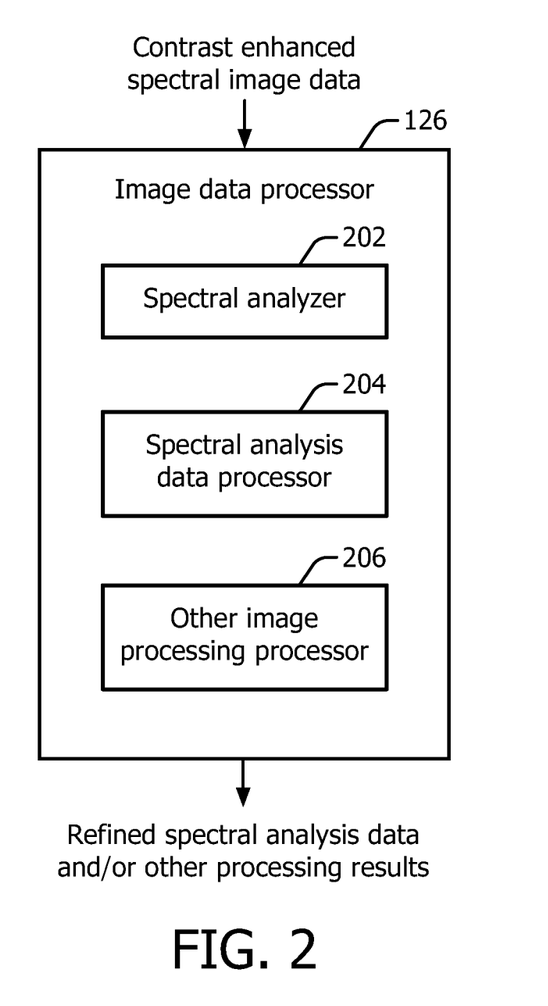
FIG. 2 schematically illustrates an example of the image data processor, which includes a spectral analysis data processor.

FIG. 2 schematically illustrates an example of the image data processor 126.

The image data processor 126 receives, as input, contrast enhanced spectral image data. In this example, the received contrast enhanced spectral image data includes cardiac spectral contrast-enhanced CT image data.

The image data processor 126 instruction(s) includes an instruction(s) for a spectral analyzer 202. The spectral analyzer 202 processes the received spectral contrast-enhanced CT scan image data, producing one or more sets of initial spectral analysis data. Such a spectral analysis can be performed on the entire scanned volume or a sub-volume thereof. The spectral analyzer 202 can use known and/or other spectral analysis techniques to process the received spectral contrast-enhanced CT scan image data.

Such techniques include generating volumetric image data sets corresponding to a quantitative contrast agent (e.g., iodine, gadolinium, etc.) map, generating volumetric image data sets corresponding to virtual non-contrast (VNC) data, virtual un-enhanced data, iodine/calcium separation, and/or other material analyses and/or identification. An example technique is discussed in Thomas et al., "Automatic lumen segmentation in calcified plaques: dual-energy CT versus standard reconstructions in comparison with digital subtraction angiography," AJR (2010).

In a variation, the spectral analyzer 126 is omitted, and the image data processor 126 receives the spectral analysis data, which is generated by a different apparatus. The spectral analysis data, as discussed herein, may be susceptible to image quality degradation, including in constricted regions of a tubular structure, for example, due the limited resolution in cardiac CT images, the partial volume effect of the contrast agent with other biological materials such as calcifications and other plaque, blooming artifact resulting from hyper-dense objects such as calcified plaque, etc.

The image data processor 126 instruction(s) includes an instruction(s) for a spectral analysis data processor 204. As described in greater detail below, the spectral analysis data processor 204, through an iterative process, updates and refines the spectral analysis data. This includes, in one instance, for each iteration, updating the spectral analysis data based at least on a contrast agent spectral response curve and a most likely tissue type for each pixel or voxel of the spectral analysis data, and calculating a relative contrast agent within each pixel, which provides an updated value for each pixel. The updated spectral analysis data of the last iteration provides the refined spectral analysis data.

The image data processor 126 instruction(s) includes an instruction(s) for an other image processing processor 204. The other image data processing processor utilizes the refined spectral analysis data in connection with other image data processing. For example, where the refined spectral analysis data includes a segmentation of a coronary artery lumen, examples of the other image data processing algorithm(s) may include a CT fractional flow reserve analysis (CT-FFR) algorithm, an Acute Coronary Syndrome (ACS) risk assessment algorithm, and/or other algorithm.

The refined spectral analysis data can improve a CT fractional flow reserve analysis (CT-FFR) and/or an Acute Coronary Syndrome (ACS) risk assessment. For example, the refined segmentation can improve the accuracy of the segmentation of the lumen, which can improve the accuracy of the CT-FFR. In another example, the refined segmentation can mitigate the blurring effect associated with conventional imaging, allowing for more accurate quantification and characterization of plaque components for ACS risk estimation.

Figure 3:
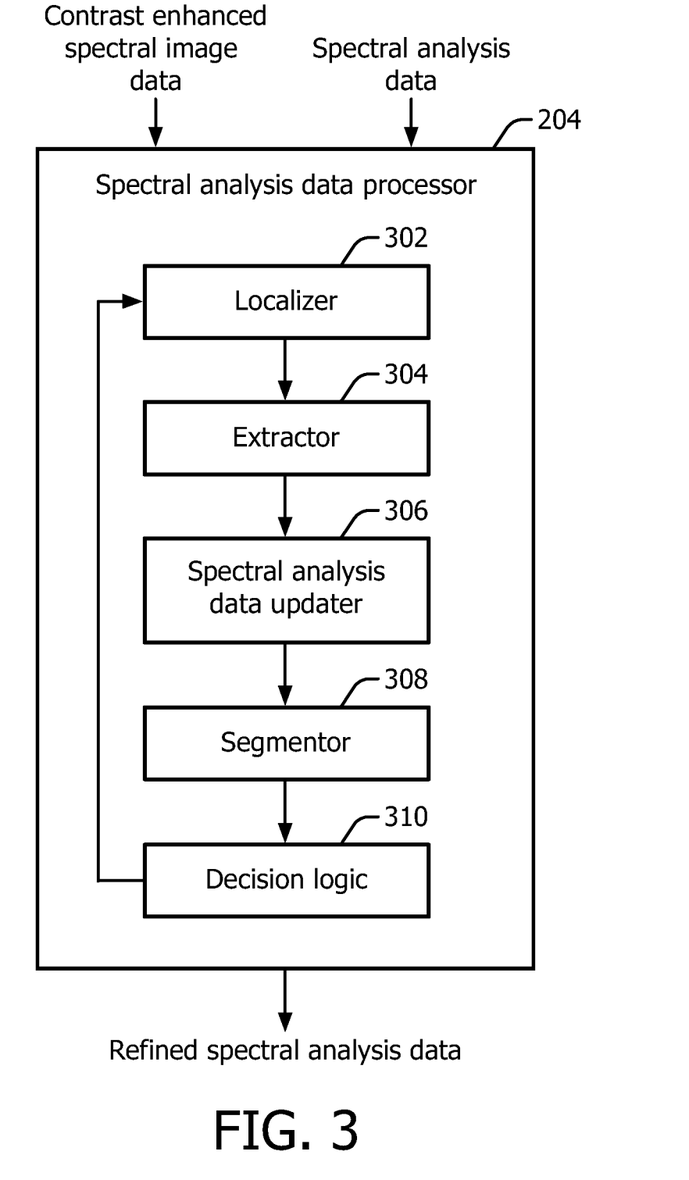
FIG. 3 schematically illustrates an example of the spectral analysis data processor, which includes a spectral analysis data updater.

FIG. 3 schematically illustrates an example of the spectral analysis data processor 204.

For explanatory purposes, the following is described in connection with coronary artery segmentation. However, it is to be understood that this example is not limiting and that other structure is also contemplated herein. For example, the following can be utilized with any tubular structure, anatomical (e.g., such as vessels) and/or non-anatomical.

The spectral analysis data processor 204 receives, as input, the contrast enhanced spectral image data and the initial spectral analysis data generated by the spectral analyzer 202. In this example, the initial spectral analysis data includes at least a contrast agent map such as an iodine map where the contrast agent is iodine. In a variation, the contrast agent map can be based on other contrast agents comprising high attenuation materials such as gadolinium, bismuth, gold and others.

The spectral analysis data processor 204 includes a localizer 302. The localizer 302 receives, as input, the initial spectral analysis data (for the first iteration) and updated spectral analysis data (from each subsequent iteration). The localizer 302 localizes the coronary arteries and/or other structure in the (initial or updated) spectral analysis data. Known and/or other, automatic (with no user interaction) and/or manual (with user interaction), approaches can be used.

The spectral analysis data processor 204 further includes an extractor 304. The extractor 304 receives, as input, the spectral analysis data with the localized the coronary arteries. The extractor 304 extracts a center-line for each coronary artery and/or other structure in the spectral analysis data. Known and/or other, automatic (with no user interaction) and/or manual (with user interaction), approaches can be used.

The spectral analysis data processor 204 further includes a spectral analysis data updater 306. The spectral analysis data updater 306 receives, as input, the spectral analysis data, the localized the coronary arteries, and the extracted center line. The spectral analysis data updater 306 updates the spectral analysis data. As briefly discussed above and as discussed in greater detail below, this include updating the spectral analysis data based on a contrast agent spectral response along the center line and a most likely tissue type for each voxel, which are used to calculate a relative contrast agent within each voxel.

The spectral analysis data processor 204 further includes a segmentor 308. The segmentor 308 receives, as input, the updated spectral analysis data. The segmentor 308 segments structure of interest from the updated spectral analysis data. Known and/or other segmentation approaches can be used. With one approach, a set of contours is applied over the spectral analysis data, which is initialized as a surface surrounding the estimated centerline. The contour can be based on a Chan-Vese minimal variance and geodesic surface models.

The above discussed approach is discussed in greater detail in Holtzman-Gazit et al., "Segmentation of thin structures in volumetric medical images," Image Processing, IEEE Transactions on 15.2 (2006): 354-363. Another approach is described in Lesage et al., "A review of 3D vessel lumen segmentation techniques: Models, features and extraction schemes," Medical image analysis 13.6 (2009): 819-845. Other approaches are also contemplated herein. From these approaches, an accurate segmentation of the coronary lumen can be achieved.

For coronary artery segmentation, the segmentor 308 can utilize the above and/or other approaches to segment the coronary artery lumen. The segmentor 308, for example, can also identify and segment plaque and/or other tissue shapes of the artery walls. This can be achieved using virtual non-contrasted (VNC) image data, where the contrast agent enhancement is removed from the contrast enhanced image data.

In one embodiment, the segmentor 308 can also improve lumen boundary estimation. For example, the spectral analysis image data and segmentation provides the mapping of the relative amount of contrast agent in each voxel in the artery. The relative amount can be different than 100% or 0% in the vicinity of the artery walls due to the partial volume effect and the limited spatial resolution. Several models can be used to estimate sharper walls and even further improved lumen segmentation.

One approach uses prior knowledge (usually by calibration) of smeared shapes of known tubes. This approach has been used for lung airway lumen and wall measurements. An example of this approach is discussed in Saba et al., "Maximizing quantitative accuracy of lung airway lumen and wall measure obtained from X-ray CT imaging," J. Appl. Physiol. (2003). Another technique applies a 3D de-convolution using a known 3D point-spread function corresponding to the imaging protocol and parameters.

The spectral analysis data processor 204 further includes decision logic 310. The decision logic 310 determines whether another iteration is to be performed based on stopping criteria. For example, the decision logic 310 invokes another iteration in response to the updated spectral analysis data not satisfying the stopping criteria. Otherwise, no more iterations are performed, and the updated spectral analysis data is output as the refined spectral analysis data.

The stopping criteria can be determined by selecting an empirical number of iterations, checking changes between successive iterations until it is sufficiently small, comparing a global figure of merit against a pre-defined threshold, and/or other approach. For other clinical applications, the approach can be extended to improve narrow blood vessel segmentation in other organs such as brain, carotids, liver, lungs and others.

Figure 4:
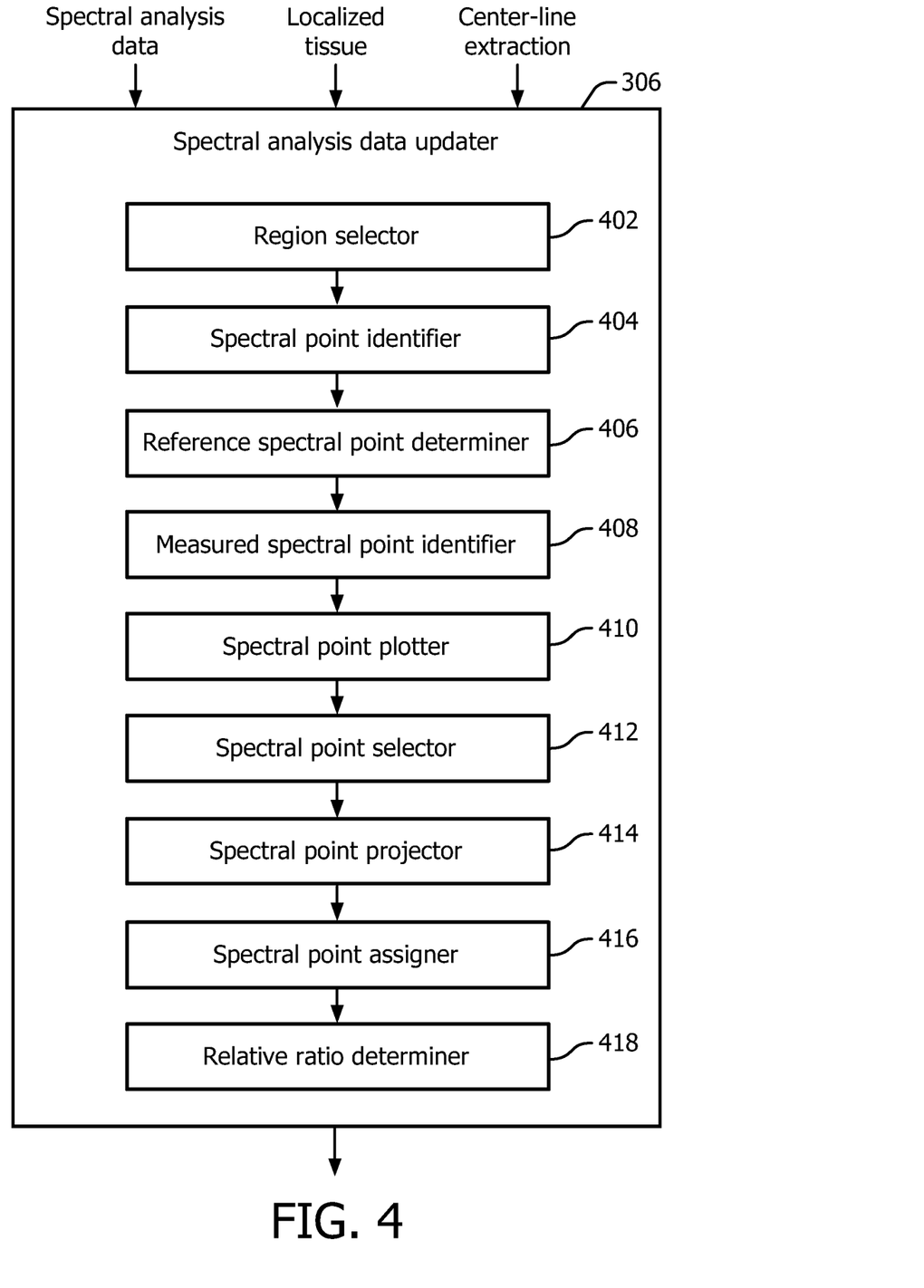
FIG. 4 schematically illustrates an example of the spectral analysis data updater.

FIG. 4 schematically illustrates an example of the spectral analysis data updater 306.

For explanatory purposes, the following is described in connection with the coronary artery segmentation discussed in FIG. 3. Similarly, it is to be understood that this example is not limiting and that other tissue is also contemplated herein.

The spectral analysis data updater 306 receives, as input, the spectral analysis data, the localized coronary arteries, and the extracted center line. In this example, similar to FIG. 2, the spectral analysis data includes a contrast agent map such as an iodine map.

The spectral analysis data updater 306 includes a region selector 402. The region selector 402 selects, using an automatic and/or manual approach, two or more regions along the coronary artery in the spectral analysis data. Generally, a selected region corresponds to a region of a tubular structure with a relatively wide cross-section. This can be determined based on a pre-determined minimal diameter threshold and/or otherwise.

Figure 5:
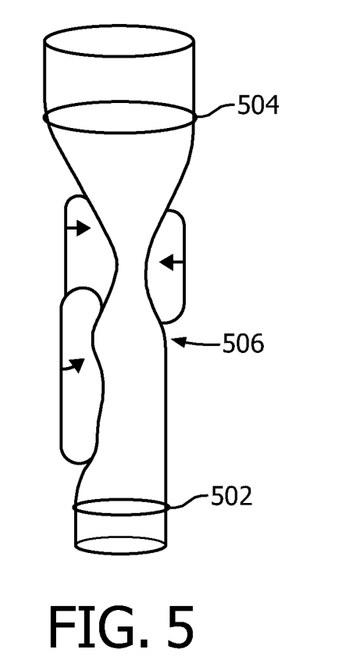
FIG. 5 shows a sub-portion of a vessel with a stenosis in which regions are identified to determine reference spectral points to determine a reference contrast agent in blood spectral response curve.

In this example, the regions provide artery sections where the lumen center has no or little partial volume or spatial resolution overlap with the walls. In these regions, the contrast agent quantification can be determined accurately using the input spectral analysis image data. FIG. 5 shows selection of two regions, 502 and 504. The two regions 502 and 504 respectively correspond to a region before a stenosis 506 and a region after the stenosis 506. In another embodiment, more than two regions are selected. Furthermore, the regions can include and/or be different from regions 502 and 504.

Figure 6:
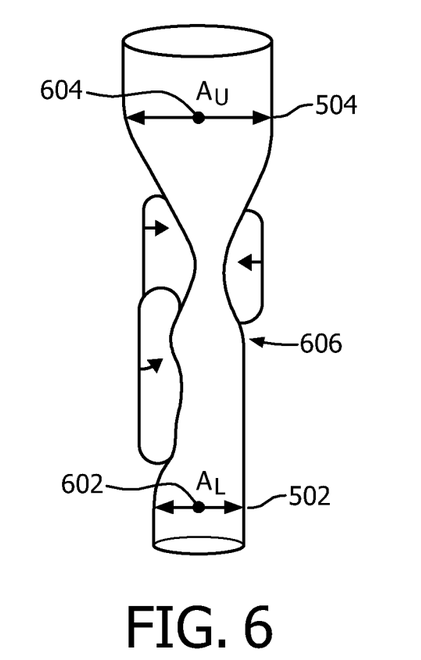
FIG. 6 shows the sub-portion of the vessel of FIG. 5 in which the reference spectral points are identified for determining the reference contrast agent in blood spectral response curve.

Returning to FIG. 4, the spectral analysis data updater 306 further includes a spectral point identifier 404. The term spectral point refers to the set of values of the different spectral images corresponding to a single pixel or voxel in the imaged volume. For instance, a spectral point can be represented as a point in the diagrams in FIGS. 8-10, which are discussed below. The spectral point identifier 404 identifies, for the selected regions 502 and 504, a spectral point for each of the selected regions 502 and 504. FIG. 6 illustrates two points $(A_L)$ 602 and $(A_U)$ 604, respectively for the two regions 502 and 504 of FIG. 5.

Returning to FIG. 4, the spectral analysis data updater 306 further includes a reference spectral point determiner 406. The reference spectral point determiner 404 determines, from the spectral points 602 and 604 identified in spectral analysis data of FIG. 5, a reference spectral point. In one instance, the reference spectral point determiner 404 generates an interpolated spectral response line (e.g., $(A_U+A_L)/2$) along the center-line. This includes narrow regions which may have partial volume and overlap with the walls, where contrast quantification may not be accurately determined only from the local data.

Figure 7:
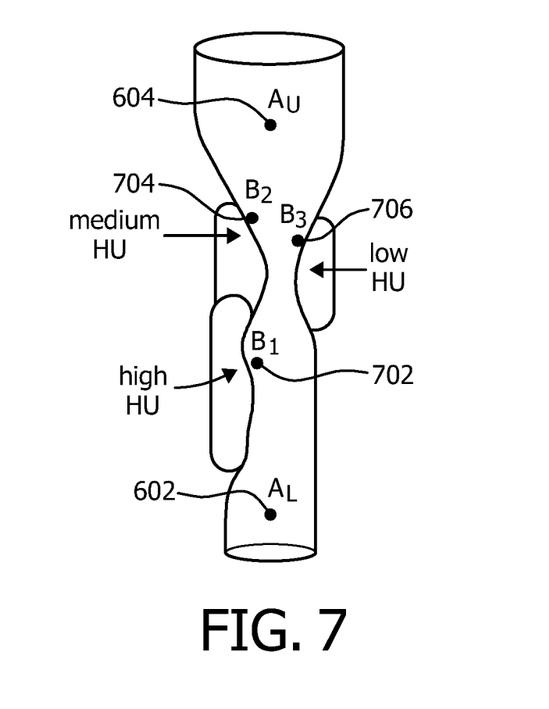
FIG. 7 shows the sub-portion of the vessel of FIG. 5 in which measured spectral points are identified.

The spectral analysis data updater 306 further includes a measured spectral point identifier 408. The measured spectral point identifier 408 identifies measured spectral points of interest within the spectral image data. FIG. 7 shows a plurality of example measured spectral points of interests $(B_1)$ 702, $(B_2)$ 704 and $(B_3)$ 706. In FIG. 7, the measured spectral points of interests $(B_1)$ 702 is adjacent to a material with a high attenuation value (represented in terms of Hounsfield Unit in FIG. 7). The measured spectral points of interests $(B_2)$ 704 is adjacent to a material with a medium attenuation value. The measured spectral points of interests $(B_3)$ 706 is adjacent to a material with a low attenuation value. For example, the high attenuation value can be caused by calcium or by a plaque-targeted contrast agent which is different than the contrast agent in the vessel lumen, the medium attenuation value can be caused by a soft tissue, and the low attenuation value can be caused by lipids.

Figure 8:
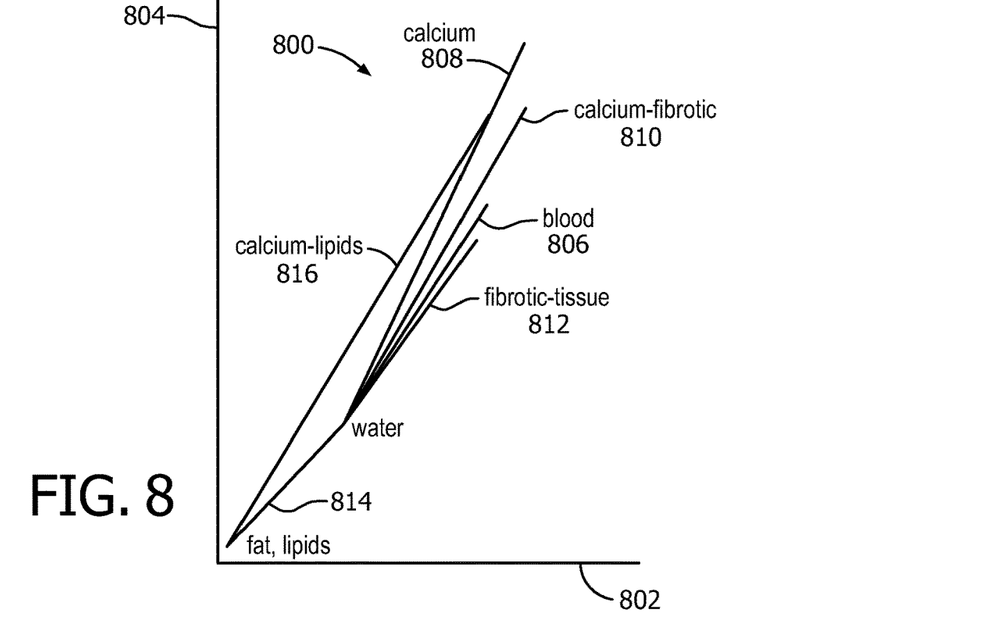
FIG. 8 shows an example spectral response graph with an example set of spectral response curves.

The spectral analysis data updater 306 further includes a spectral point plotter 410. The spectral point plotter 410 plots the reference and the measured spectral points on an energy spectral graph. An example of a dual energy low energy—high energy graph is shown in FIG. 8. In FIG. 8, a graph 800 includes a first axis 802, which represents the attenuation of a pixel in a first higher energy image of the spectral image data, and a second axis 804, which represents the attenuation of the same pixel in a second lower energy image of the spectral image data. In this example, the low energy and the high energy axes are in terms of Hounsfield units (HUs). In another example, the low energy and the high energy axes may be in terms of other units and can represent values such as photoelectric compton-scattering decomposition, virtual monochromatic images, or material basis representation.

In FIG. 8, a first spectral curve 806 represents a blood-water curve, a second spectral curve 808 represents a calcium-water curve, a third spectral curve 810 represents a calcium/fibrotic-water curve, a fourth spectral curve 812 represents a fibrotic tissue-water curve, a fifth curve 814 represents a fat, lipids-water spectral curve, and a sixth curve 816 represents a calcium/lipids-water curve. The particular curves of such a graph can be different and represent the tissue of interest. Although the graph 800 is for two energies, it is to be understood that more than two energies can be considered. For example, N energies (where N is a positive integer) can be considered. In such an example, the graph 800 can include a N-dimensional (N-D) graph.

Figure 9:
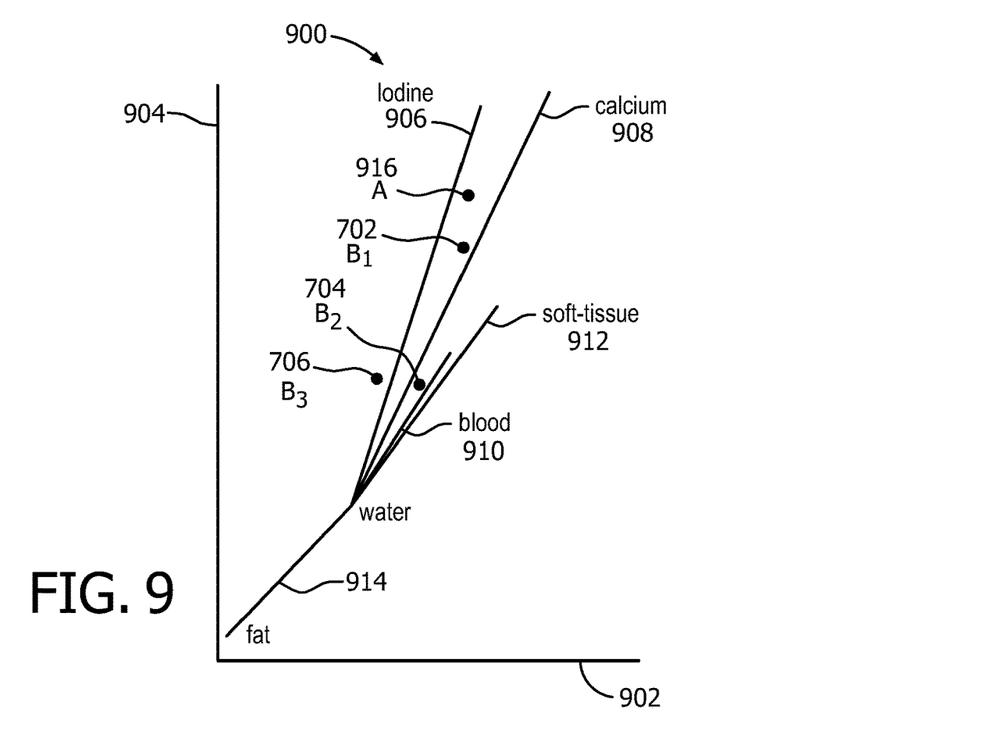
FIG. 9 shows an example spectral response graph that includes the reference and measured spectral response point of FIG. 7 and a set of spectral response curves.

FIG. 9 shows a dual (low and high) energy graph 900 in connection with the spectral points of FIG. 7. In FIG. 9, a first axis 902 represents the attenuation of a pixel in a higher energy image and a second axis 904 represents the attenuation of the same pixel in a lower energy image. In FIG. 9, a first spectral curve 906 represents an iodine-water curve, a second spectral curve 908 represents a calcium-water curve, a third spectral curve 910 represents a blood-water curve, a fourth spectral curve 912 represents a soft tissue-water curve, and a fifth curve 914 represents a fat-water spectral curve. An iodine-blood spectral point (A) 916 represents a reference spectral point. The spectral points $B_1$, $B_2$, and $B_3$ correspond to the measured spectral points of interests ($B_1$) 702, ($B_2$) 704 and ($B_3$) 706 of FIG. 7.

Returning to FIG. 4, the spectral analysis data updater 306 further includes a spectral line selector 412. The spectral line selector 412 selects, for each pixel, a spectral line corresponding to a most probable tissue type for the pixel. This, in one instance, can be done based on a virtual non-contrast image and a model. The virtual non-contrast image provides data in which it is easier to determine automatically if calcium is involved or not in a certain region.

Figure 10:
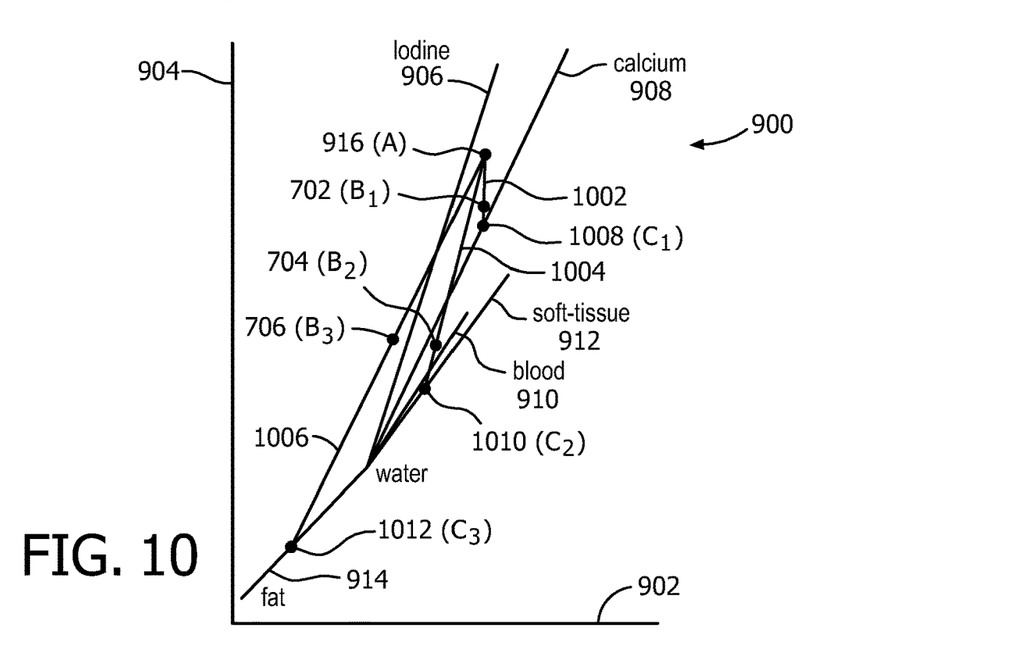
FIG. 10 shows the example of FIG. 9 with lines projected from the spectral response point through the measured spectral response points to the spectral response curves.

The spectral analysis data updater 306 further includes a spectral point projector 414. The spectral point projector 414 projects, for each pixel, the spectral points. In one instance, for this, the spectral point projector 414 projects a line from the reference spectral point (A) 916, through each of the measured points ($B_1$) 702, ($B_2$) 704 and ($B_3$) 706, to the corresponding selected spectral curve. This is shown in FIG. 10, which shows lines 1002, 1004, 1006 projected from the reference spectral point (A) 916, through the measured points ($B_1$) 702, ($B_2$) 704 and ($B_3$) 706 to the selected curves 908, 912, and 914.

Returning to FIG. 4, the spectral analysis data updater 306 further includes a spectral point assigner 416. The spectral point assigner 416 assigns, for each pixel, a point on the selected curve where the projected line intersects. This is also shown in FIG. 10, where the spectral line assigner 416 assigns points ($C_1$) 1008, ($C_2$) 1010 and ($C_3$) 1012 based on the projections 1002, 1004, 1006 from the reference spectral point (A) 916, through of the measured points ($B_1$) 702, ($B_2$) 704 and ($B_3$) 706 to the selected curves 908, 912, and 914. In this example, the spectral point ($B_1$) 702 projected onto the calcium (bone)—water line 908. In another example, the spectral point ($B_1$) 702 can be projected onto blood-water line 910, the soft tissue-water line 912, and/or other spectral response line.

Returning to FIG. 4, the spectral analysis data updater 306 further includes a relative ratio determiner 418. The relative ratio determiner 418 calculates a relative ratio R of contrast agent within a voxel (e.g., relative to the assumed contrast agent-in-blood value). In one instance the ratio is determined by: $R=|B-C|/|A-C|$, which is the ratio of the absolute distances, where A, B and C are vectors; each one comprises N elements, where N is the number of different spectral images in the analyzed data. The spectral image data updater 306 outputs the relative contrast agent-in-blood values as the updated spectral analysis image data.

As discussed in connection with FIG. 3, the decision logic 310 determines whether another iteration is performed or the updated spectral analysis data is output as the refined spectral analysis data. As discussed in connection with FIG. 2, the refined spectral analysis data can be utilized in connection with other processing such as CT-FFR, ACS risk assessment, etc.

Figure 11:
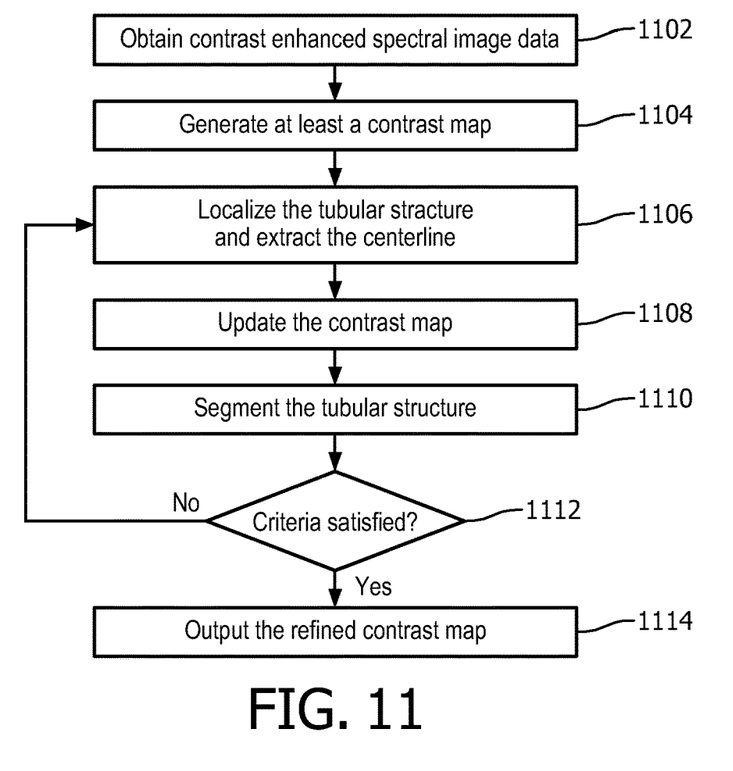
FIG. 11 illustrates an example method in accordance with the embodiments described herein.

FIG. 11 illustrates an example method in accordance with the embodiments described herein.

It is to be appreciated that the ordering of the acts in the methods described herein is not limiting. As such, other orderings are contemplated herein. In addition, one or more acts may be omitted and/or one or more additional acts may be included.

At 1102, contrast enhanced spectral image data, which includes image data with voxels representing a tubular, is obtained.

At 1104, at least a contrast map is generated from the contrast enhanced spectral image data. This may be achieved using a model. Other information such as iodine/calcium separation, a VNC image, etc. may also be generated.

At 1106, the tubular structure is localized and center-lines of the localized tubular structure is extracted. For the first iteration, this is based on the initial iodine map. In subsequent iterations, this is based on the most recent updated iodine map.

At 1108, the contrast map is updated based on the localized tubular structure, the extracted center-lines, and a multi-energy graph model. The updated contrast map can be used to identify partial iodine in partial volume regions, provide an analysis of material build up and tubular structure walls, and refine VNC images.

At 1110, the tubular structure is segmented based on the updated contrast map and a tubular structure segmentation model. This may include lumen segmentation using active-contour functional applied on the refined contrast map, improved lumen boundary estimation based on the refined contrast map and the material analysis, a correction model for partial volume and limited resolution effects, plaque region localization for segmentation, etc.

At 1112, it is determined if stopping criteria has been satisfied. Examples of the stopping criteria include an empirical number of iterations, a difference between results of successive iterations, comparison with a global figure of merit against, and/or other approach.

If the stopping criteria has not been satisfied, then acts 1106 to 1110 are repeated. However, if the stopping criteria has been satisfied, then at 1114 the refined contrast map is output. As discussed herein, the refined contrast map can be used in connection with other processing of the image.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
obtaining contrast enhanced spectral image data that includes voxels representing a tubular structure;
generating at least a contrast map based on the obtained contrast enhanced spectral image data;
localizing the tubular structure in the contrast map;
extracting a center-line of the localized tubular structure;
generating an updated contrast map by calculating a relative contrast agent within each voxel, the calculating being based on:
the contrast map;
the localized tubular structure;
a contrast agent spectral response along the extracted center-line of the localized tubular structure; and
a most probable tissue type for each voxel, the most probable tissue type being based on a spectral model; and
segmenting the tubular structure based on the updated contrast map.

2. The method of claim 1, wherein the tubular structure is a vessel.

3. The method of claim 2, wherein the spectral model is a multi-energy graph with spectral curves for a plurality of predetermined different types of material.

4. The method of claim 2, wherein the updated contrast map includes partial contrast agent in partial volume regions.

5. The method of claim 1, further comprising:
generating iodine/calcium separation information based on the obtained contrast enhanced spectral image data; and
generating updated iodine/calcium separation information based on the contrast map, the localized tubular structure, the extracted center-line, and the spectral model.

6. The method of claim 5, further comprising:
generating virtual non-contrast image based on the obtained contrast enhanced spectral image data; and
generating an updated virtual non-contrast image based on the contrast map, the localized tubular structure, the extracted center-line, and the spectral model.

7. The method of claim 1, further comprising:
determining if stopping criteria has been met; and, in response to the determining the stopping criteria has not been met:
localizing the tubular structure in the updated contrast map;
extracting a second center-line from the tubular structure localized in the updated contrast map;
generating a second updated contrast map based on the tubular structure localized in the updated contrast map, the second extracted center-line, and the spectral model.

8. The method of claim 1, further comprising:
determining if stopping criteria has been met; and
outputting the updated contrast map as a refined contrast map in response to the determining the stopping criteria has been met.

9. The method of claim 1, further comprising:
applying an active-contour functional to segment a lumen of the tubular structure.

10. The method of claim 1, further comprising:
estimating a boundary of a lumen of the tubular structure based on the updated contrast map and a material analysis.

11. The method of claim 1, further comprising:
determining a partial volume correction model; and
employing the partial volume correction model to correct for partial volume effects in the updated contrast map.

12. The method of claim 1, further comprising:
localizing a plaque region of the tubular structure based on the updated contrast map; and
segmenting the plaque region from the updated contrast map.

13. The method of claim 1, wherein the tubular structure is a coronary artery, and further comprising:
performing CT fractional flow reserve analysis using the segmented tubular structure.

14. The method of claim 1, wherein the tubular structure is a coronary artery, and further comprising:
performing an Acute Coronary Syndrome risk assessment using the segmented tubular structure.

15. A computing system, comprising:
a spectral analyzer that receives contrast enhanced spectral image data and generates a spectral analysis data based thereon, wherein the spectral analysis data includes a contrast map; and
a spectral analysis data processor that refines the spectral analysis data, generating refined spectral analysis data, the spectral analysis data processor, comprising:
a localizer that localizes a tubular structure in the spectral analysis data;
an extractor that extracts a center-line of the localized tubular structure;
a spectral analysis data updater that generates updated spectral analysis data by calculating a relative contrast agent within each voxel the calculating being based on:
the spectral analysis data;
the localized tubular structure;
a contrast agent spectral response along the extracted center-line of the localized tubular structure; and
a most probable tissue type for each voxel, the most probable tissue type being based on a model; and
a segmentor that segments the tubular structure based on the updated spectral analysis data.

16. The computing system of claim 15, the spectral analysis data processor, comprising:
decision logic that triggers a further update of the updated spectral analysis data is based on pre-determined stopping criteria.

17. The computing system of claim 16, the spectral analysis updater, comprising:

a region selector that selects two or more regions along the tubular structure corresponding to regions with a diameter greater than a pre-determined minimal diameter threshold;

a spectral point identifier that identifies, for each of the selected regions, a spectral point;

a reference spectral point determiner that determines a reference spectral point based on the identified spectral points;

a measured spectral point identifier that identifies measured spectral points of interest within the spectral image data;

a spectral point plotter that plots the reference and the measured spectral points in an energy spectral graph;

a spectral line selector that selects, for each pixel, a spectral line corresponding to a most probable tissue type for the pixel;

a spectral point projector that projects, for each pixel, the spectral points from the reference spectral point, through each of the measured points, to the corresponding selected spectral curve;

a spectral point assigner that assigns, for each pixel, a point on the selected curve where the projected line intersects; and a relative ratio determiner that determines a relative ratio of contrast agent within a voxel based on the reference spectral point, the measured spectral points, and the assigned points, wherein the spectral analysis updater generates the updated spectral analysis data based on the relative ratios.

18. The computing system of claim 15, further comprising:

an image processor that performs a CT fractional flow reserve analysis based on the segmented the tubular structure.

19. The computing system of claim 15, further comprising:

a processing processor that performs an Acute Coronary Syndrome risk assessment based on the segmented the tubular structure.

20. A non-transitory computer-readable medium having one or more executable instructions stored thereon, which, when executed by processor circuitry, cause the processor circuitry to perform a method, comprising:

obtaining contrast enhanced spectral image data that includes voxels representing a tubular structure;

generating at least a contrast map based on the obtained contrast enhanced spectral image data;

localizing the tubular structure in the contrast map;

extracting a center-line of the localized tubular structure;

generating an updated contrast map by calculating a relative contrast agent within each voxel, the calculating being based on:

the contrast map;

the localized tubular structure;

a contrast agent spectral response along the extracted center-line of the localized tubular structure; and a most probable tissue type for each voxel, the most probable tissue type being based on a spectral model; and segmenting the tubular structure based on the updated contrast map.

* * * * *